United States Patent [19]

Sarunac

[11] Patent Number: 4,997,574
[45] Date of Patent: Mar. 5, 1991

[54] STAGED BOUNDARY LAYER TREATMENT METHOD AND SYSTEM FOR BIOFOULING CONTROL

[75] Inventor: Nenad Sarunac, Catasauqua, Pa.
[73] Assignee: Lehigh University, Bethlehem, Pa.
[21] Appl. No.: 401,781
[22] Filed: Sep. 1, 1989
[51] Int. Cl.⁵ .................... G01N 17/00; C02F 1/76
[52] U.S. Cl. .................... 210/739; 73/61.2; 137/93; 210/96.1; 210/199; 210/752; 210/754; 210/764; 422/28
[58] Field of Search ........... 73/61 R, 61.2, 61.1 R, 73/861.05; 210/96.1, 199, 739, 752-755, 764; 364/500, 502, 509, 510; 137/92, 93; 422/14, 28, 37

[56] References Cited

U.S. PATENT DOCUMENTS

| | | | |
|---|---|---|---|
| 3,913,378 | 10/1975 | Hausler | 73/61.2 |
| 4,339,945 | 7/1982 | Knudsen et al. | 73/61.2 |
| 4,346,587 | 8/1982 | Brindak | 73/61.2 |
| 4,570,492 | 2/1986 | Walsh | 73/861.05 |
| 4,631,173 | 12/1986 | Muller et al. | 422/28 |
| 4,686,853 | 8/1987 | Sugam et al. | 73/61.2 |
| 4,896,478 | 1/1990 | Reiter | 422/28 |
| 4,910,999 | 3/1990 | Eaton | 73/61.2 |

FOREIGN PATENT DOCUMENTS

| | | | |
|---|---|---|---|
| 54-104638 | 8/1979 | Japan | 210/739 |
| 57-187090 | 11/1982 | Japan | 210/764 |

OTHER PUBLICATIONS

Ciallela et al, "Use of Hot Scale Condensers for Biofouling Measurement and Control", 1975.

Primary Examiner—Frank Spear
Assistant Examiner—Joseph Drodge
Attorney, Agent, or Firm—Oblon, Spivak, McClelland, Maier & Neustadt

[57] ABSTRACT

A method and system for biofouling control of fluid containing structure of susceptible biofouling, wherein chlorine, hot water and/or some other control agent is injected by plural stages into the boundary layer, and chlorine residual, water temperature, or some other respective control parameter is maintained in the boundary layer just upstream of the next injection point.

18 Claims, 9 Drawing Sheets

STAGED BOUNDARY LAYER TREATMENT METHOD AND SYSTEM FOR BIOFOULING CONTROL

BACKGROUND OF THE INVENTION

1. Field of the Invention

The present invention relates to a method and system for biofouling control in, for example, the intake structure of a power plant.

2. Discussion of Background

A major problem in power plant cooling is biofouling—the deposition of organic material on cooling system surfaces. The detrimental effects of biofouling are reduced heat transfer capability in condensers, increased pressure drop or lower flow, and accelerated corrosion. The mechanisms of biofouling are complex, involving biological, physical, and chemical interactions. Its proliferation is dependent on several factors: water quality, water-borne substances and organisms, plant process conditions, interactions with other cooling system fouling phenomena, and the control measures employed.

Because of low to moderate flow velocities, isolated pockets of quiescent zones, and warm temperatures in the condensers, a plant cooling system provides an ideal environment for biological colonization and growth. Two forms of biofouling are significant: microbiological fouling of heat exchangers and macroinvertebrate fouling of the intake structure. Organisms responsible for microbiological fouling include: slime and alga. Macroinvertebrates include: mussels, barnacles, oysters and clams.

It has been determined that microbiological fouling is a dominant problem, representing approximately 70 percent of those power plant units which experienced biofouling in one form or another. In recent years, episodes of macroinvertebrate or macrofouling have risen and have become the second most important cooling system biofouling control issue in the electric power industry.

The penalties and costs associated with impaired condenser operations are substantial. They include increased fuel consumption, replacement power costs, condenser cleaning costs, and loss of availability. It is estimated that the effect of biofouling on unit availability for fossil-fired power plants over 600 MW is a 3.8 percent loss in unit availability directly attributable to poor reliability of condenser systems. The loss in availability of a typical baseload 600 MW coal unit cost an average of $500,000 a day in 1982. Availability losses from condenser problems are usually in the nature of partial load reductions. The modular nature (divided water boxes) of most condensers permits inspection, leak detection, tube plugging, and condenser cleaning while the unit is on-line.

Performance losses resulting from tube blockage and cooling water flow reductions are also significant. The direct effects of these macrofouling-based problems can only be determined on a unit by unit basis. The effects may also vary with time as a result of fouling seasons. If these effects can be correlated with an annual yearly increase in back pressure, the economic impact for typical units can be determined. It is not unreasonable to assume an average yearly increase of 0.3-inch Hg which correlates to annual replacement energy costs of approximately $800,000 for a 1150 MWe nuclear unit, and approximately $95,000 for a 600 MWe coal fired fossil unit.

Since the 1920's, gaseous chlorine or liquid hypochlorite solutions have been used to control both microbiological and macrobiological fouling at power plants. Chlorine is a powerful oxidizing agent and an effective bactericide. It eliminates bacterial slime through its toxicity to the microorganisms and through its chemical reaction with the organic substances forming the slime matrix. Chlorine is effective in controlling macrobiological fouling by having direct toxic effects on adult organisms, by inhibiting the settlement of larval stages, and by weakening the mechanisms by which the organisms remain attached to the cooling system substrates.

For the effective microbiofouling control chlorine is applied to power plant cooling water on an intermittent basis. Dosing frequency, duration, and concentration vary with the quality of cooling water, temperature, water velocity, and the magnitude of the biofouling problem. Consequently, the minimum amount of chlorine needed for adequate biofouling control is site-specific and can vary from season to season. Because waters high in organic matter or inorganic reducing agents will rapidly diminish the levels of the biocidally active form of chlorine through oxidation reactions (chlorine-demand reactions), this necessitates the use of higher initial concentrations.

The chlorination procedures necessary for the control of macrobiological fouling depend on the type of organisms which must be eliminated. To control soft-bodied organisms such as hydroids, sponges, and bryozoans, chlorine doses sufficiently high enough to generate residuals of 1 to 3 mg/l, and applied three times per day for 1 to 2 hours have been used. To control hard-shelled organisms such as mussels, low-level continuous chlorination (producing residuals of 0.02 to 1.0 mg/l), particularly during seasons when the animals reproduce, has been found to be effective.

The conventional chlorination practice for macrobiofouling control relies on flushing large volumes of chlorinated water through the circulating water system and on maintaining a free chlorine residual at the condenser outlet, as shown in FIG. 1. Part of the injected chlorine is consumed as the biological chlorine demand in reactions with the macrobiogrowth at the solid surface, some is consumed in the chlorine demand reactions of the water in the boundary layer, and some is convected and diffused in the directions parallel to and normal to the solid surface. Chlorine, convected and diffused normal to the wall, is diluted with the main water flow and consumed in chlorine demand reactions of the main cooling water flow. Chlorine, convected and diffused parallel to the wall, is gradually consumed in the biological chlorine demand reactions with the macrobiogrowth at the solid wall, and in the chlorine demand reactions of the water in the boundary layer. Therefore, at some distance from the injection point, the chlorine residual will reach a value below which the macrobiofouling control is not effective. If the distance between the injection point and the point at which the minimum chlorine residual is maintained increases, the applied chlorine dose must increase to compensate for the larger losses, and vice versa. Only that part of the chlorine dose which reacts with the biogrowth at the wall is "responsible" for antifouling control. Chlorine consumed in the demand reactions represents the loss.

An improved chlorination practice for macrobiofouling control is to maintain a free residual at the condenser inlet box, as shown in FIG. 2.

The applied chlorine dose can further be reduced in cases where macrobiofouling of the intake conduit does not occur due to high water velocities. In such cases, for macrobiofouling control it would be sufficient to maintain a free chlorine residual at the conduit inlet, as shown in FIG. 3.

Spatial variations of residual chlorine concentration in the power plant cooling systems of FIGS. 1-3 are shown in FIG. 4. Since the chlorine demand of the water in the condenser is not treated, the applied chlorine dose and the residual in the discharge are lower for the system of FIG. 2 than for the system of FIG. 1, as evident from FIG. 4. The applied chlorine dose is reduced in the system of FIG. 3 because the chlorine demand of the water in the conduit and in the condenser is not treated. Because of this, the total residual concentration at the compliance point is lower than for the other conventional chlorination practices.

Thus, as is evident from FIGS. 1-3, the conventional chlorination practices are to inject chlorine into the flow near the wall and to maintain the chlorine residual farther along in the main flow, either at the condenser exit or inlet, or at the conduit inlet. The chlorination practices described above rely on treating the entire water volume with chlorine. The total amount of chlorine used in the conventional chlorination practices is high because a large portion of the applied chlorine (e.g., oxidation, decomposition, etc.) dose is consumed in the natural chlorine demand reactions within the entire volume of water, and is converted into biologically much less active and effective forms than the free chlorine.

SUMMARY OF THE INVENTION

Accordingly, one object of this invention is to provide a new and improved method and system for biofouling control in the intake structure of, for example, a power plant, in which chlorine residual or some other selected control parameter is maintained close to the wall, so that the effects of dilution with the main water flow, and consumption in the demand reactions of the main cooling water flow are minimized, resulting in a reduction of the overall chlorine or control agent dose.

Another object is to provide a method and system as above noted, wherein the distance between the injection point and the point where the residual is maintained is short, thus resulting in a decrease in chlorine or other control agent losses and, consequently, a decrease in the required, local chlorine or other control agent dose.

A further object of this invention is to provide a method and system as above noted, wherein only the boundary layer near the wall is treated with the full chlorine or other control agent dose.

Yet another object of this invention is to provide a method and system as above noted, wherein the chlorine residual or other control parameter at the compliance point is considerably lower due to large dilution of the treated boundary layer with the main cooling water flow, and due to the biological demand for chlorine or other control agent in the condenser.

These and other objects are achieved according to the present invention by providing a novel method and system for biofouling control of the intake structure of, for example, a power plant, wherein a biofouling control agent is injected by plural stages into the boundary layer, and control agent residual is maintained in the boundary layer just upstream of the next injection point.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
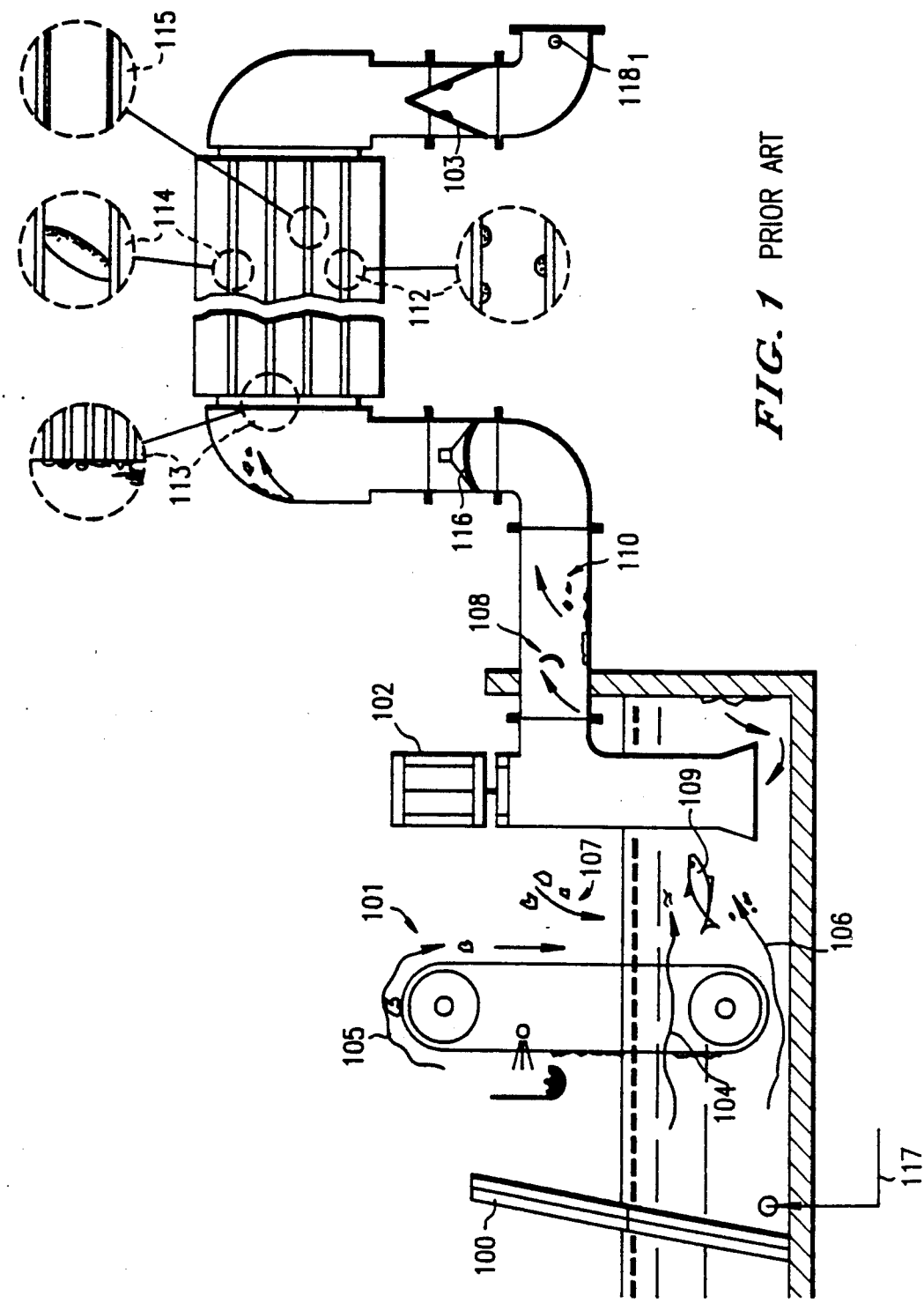
FIGS. 1, 2 and 3 are schematic illustrations of conventional biofouling chlorination practices, wherein chlorine residual is maintained at the condenser outlet, condenser inlet and conduit inlet, respectively.
Figure 2:
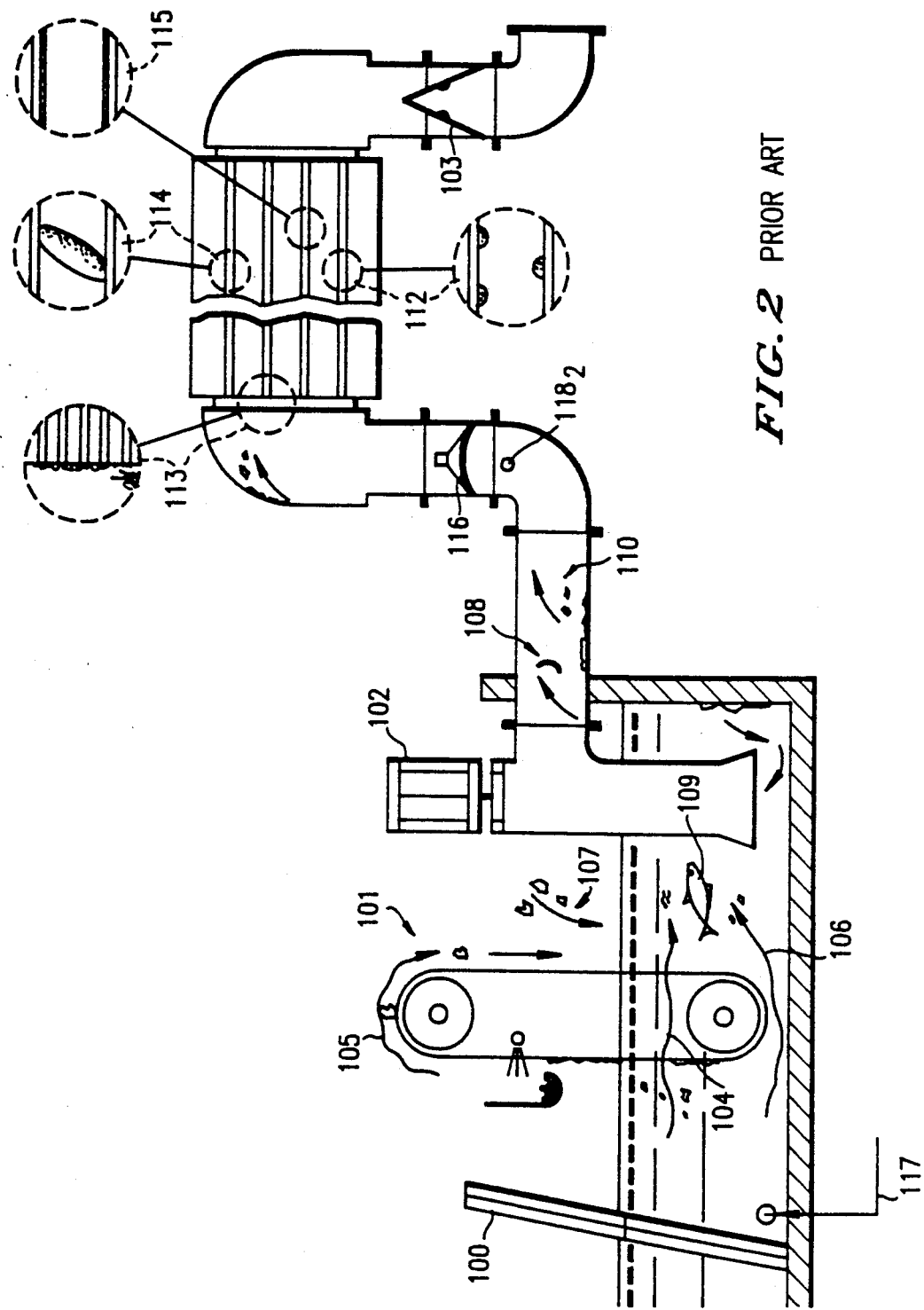
Figure 3:
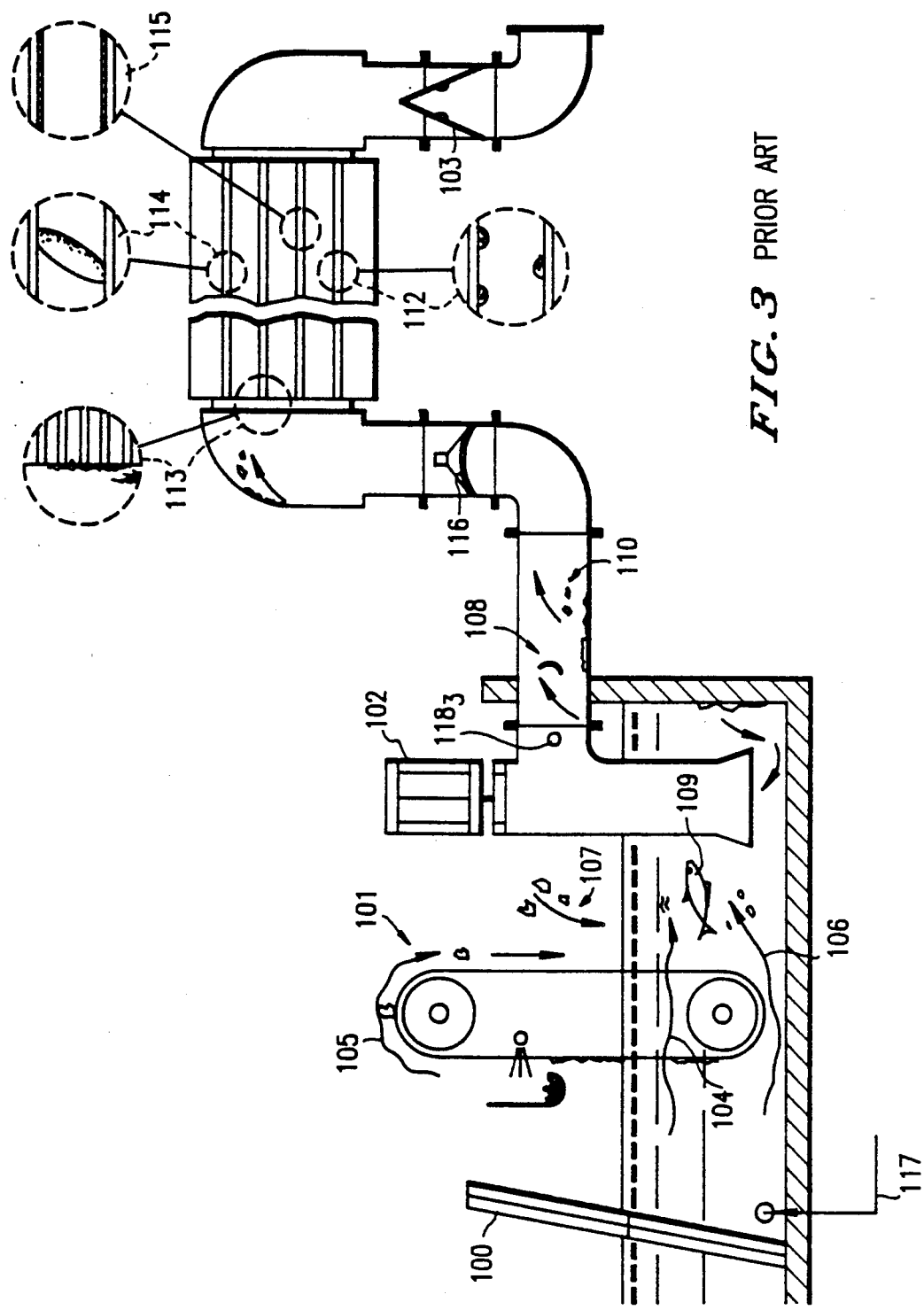
Figure 4:
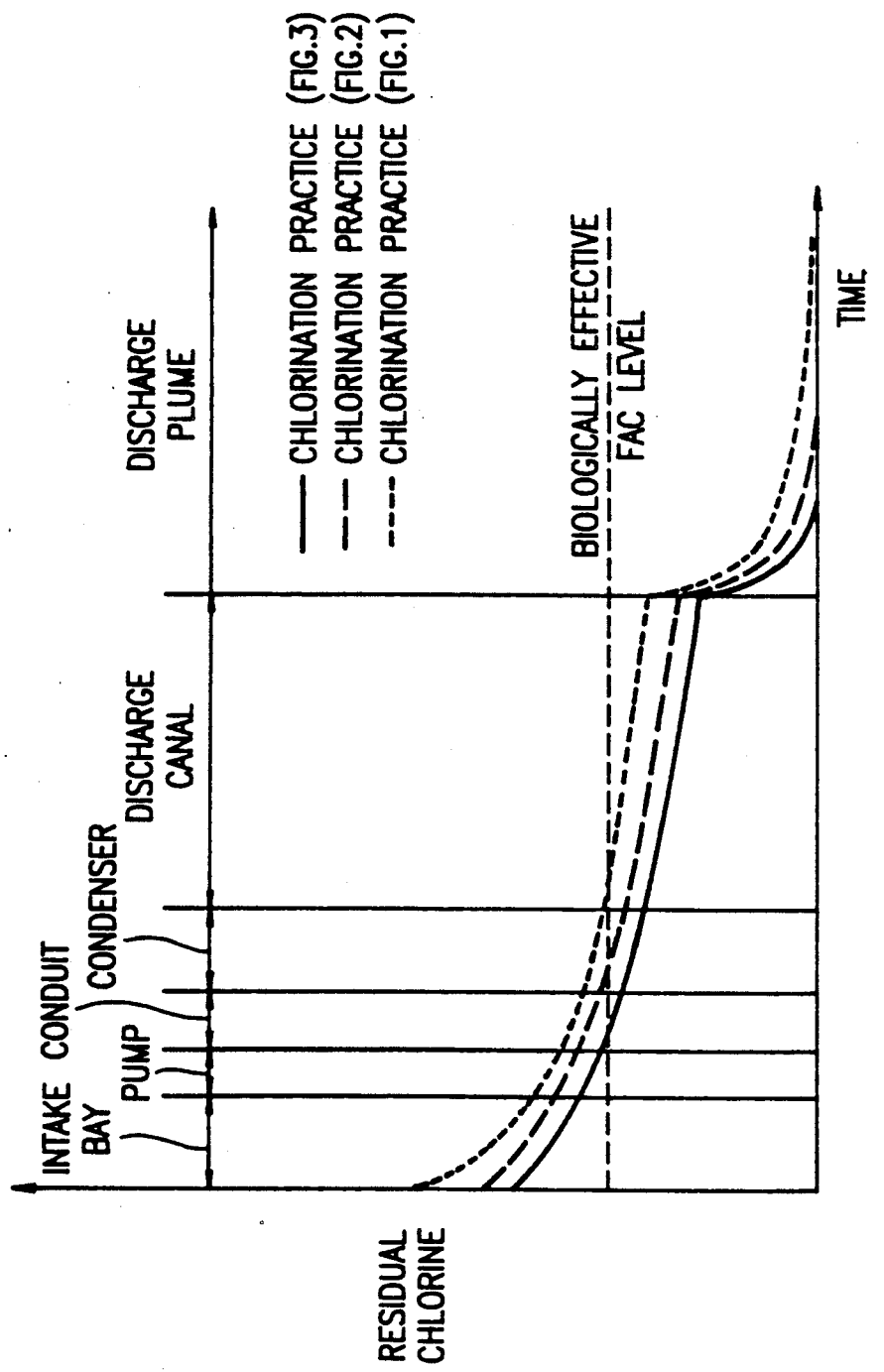
FIG. 4 is a graph comparing the variation of residual chlorine concentrations in a power plant cooling system, of each of the conventional practices shown in FIGS. 1-3.
Figure 5:
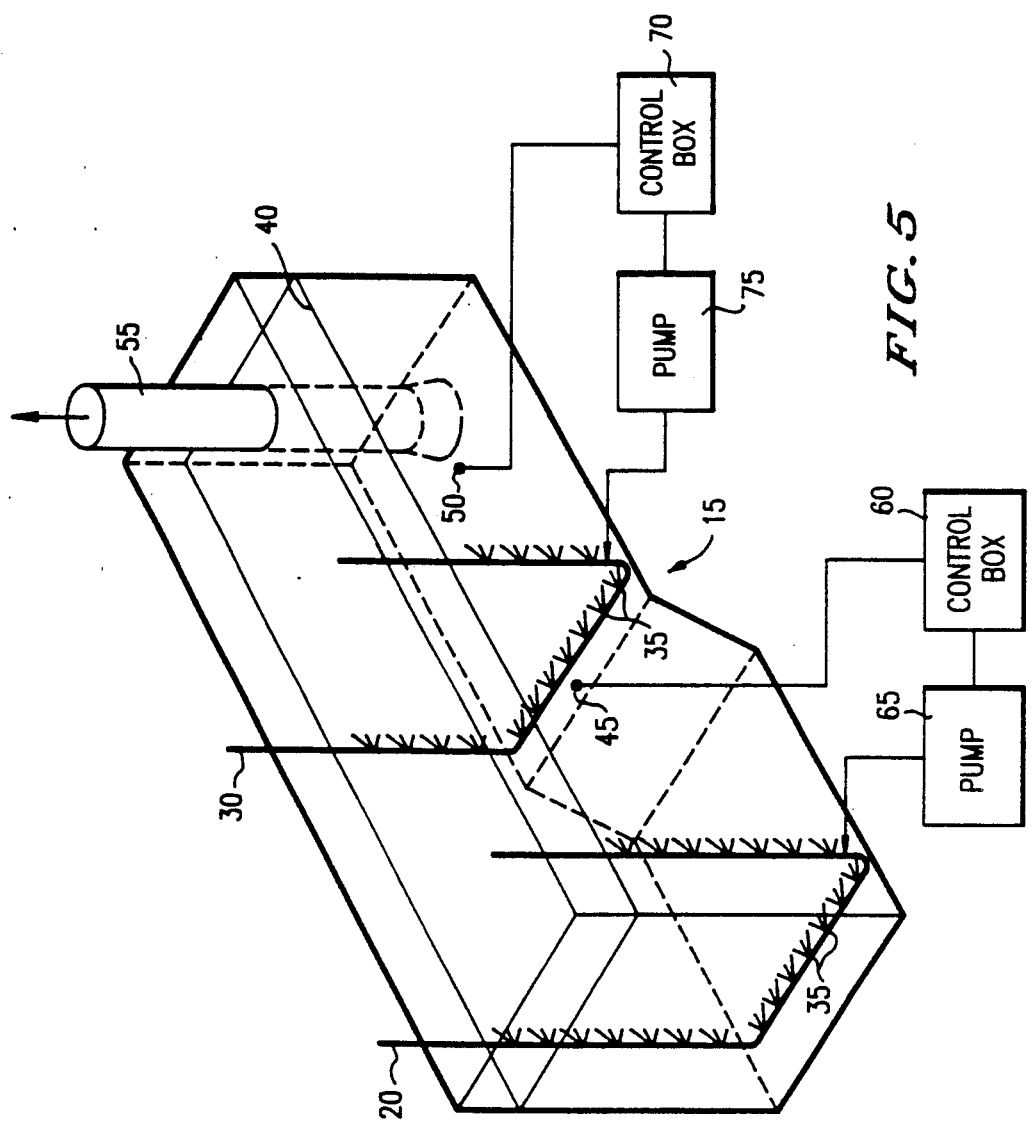
FIG. 5 is a schematic illustration of a two stage boundary layer chlorine injection system according to the present invention.

Referring now to the drawings, wherein like reference numerals indicate identical or corresponding parts throughout the several views, the new chlorination approach according to the present invention, as shown in FIG. 5, is applied to the intake bay 15 of the power plant cooling system, and includes a first chlorine injection stage 20, and at least a second chlorine injection stage 30, each of which includes plural chlorine injection nozzles 35 spaced around the periphery of the intake bay 15 below the coolant level 40. As shown in FIG. 5, immediately preceding the second chlorine injection stage 30 is located a measurement point 45 at which point free available chlorine (FAC) residual is maintained. The measurement point 45 is located in the boundary layer immediately preceding the second chlorine injection stage 30. Data from measurement point 45 is applied to control box 60 which controls pump 65 coupled to the injectors 35 of stage 30. A second measurement point 50 is located in the boundary layer immediately preceding the outlet conduit 55 of the intake bay 15 and is used to control chlorine injection by the injection nozzles 35 of the second stage 30 by means of control box 65 and pump 70. Although only two chlorine injection stages and two measurement points are shown, it should be understood that more than two injection stages each including one or more associated measurement points in the boundary layer are possible, for example—one measurement point adjacent each wall, depending upon the length of the intake bay 15. For typical intake bay dimensions of 40 feet in length, 25 feet in depth and 12 feet in width, the use of 2 to 4 chlorine injection stages each having one measurement point is anticipated. If more than one measurement point is used, selected injectors 35 can be controlled based on data obtained from a respective measurement. Alternatively, data from the measurement points can be combined to derive a simple average, or a weighted average, and chlorine injection can then be controlled at individual injectors 35 accordingly. If a weighted average is used, sensors could be located at measurement points in the boundary layer adjacent each wall, and the injectors adjacent each wall could be controlled primarily based on the measured data obtained adjacent the same wall, with a weighted secondary contribution from data obtained at other measurement points in dependence on the distance of the other measurement points from, for example, the measurement point adjacent the same wall.

The new chlorination method, referred to as staged boundary layer chlorination is based on treating the boundary layer with chlorine and not the whole volume of water. It relies on staged injection of chlorine into the boundary layer and on maintaining a Free Available Chlorine (FAC) residual upstream of the next injection stage, as shown in FIG. 5. Due to staged injection of chlorine, the distance between the injection point and the location where FAC residual is maintained is short. Therefore, the time available for chlorine demand reactions is also short. Consequently, the portion of the chlorine dose consumed in natural chlorine demand reactions will be smaller, compared to the conventional or improved chlorination practices. This will result in a reduction of the specific chlorine dose (the amount of chlorine needed per unit volume of water). More importantly, only the boundary layer near the wall will be treated with the full chlorine dose, and not the entire volume of water. As a result, the absolute chlorine dose (the amount of chlorine needed per total volume of water) will be significantly smaller, compared to the conventional chlorination practices. The chlorinated boundary layer will combine with the much larger volume of unchlorinated water flowing through the intake. This will result in a large dilution and will permit many of the chlorine residuals to form harmless compounds.

Figure 6:
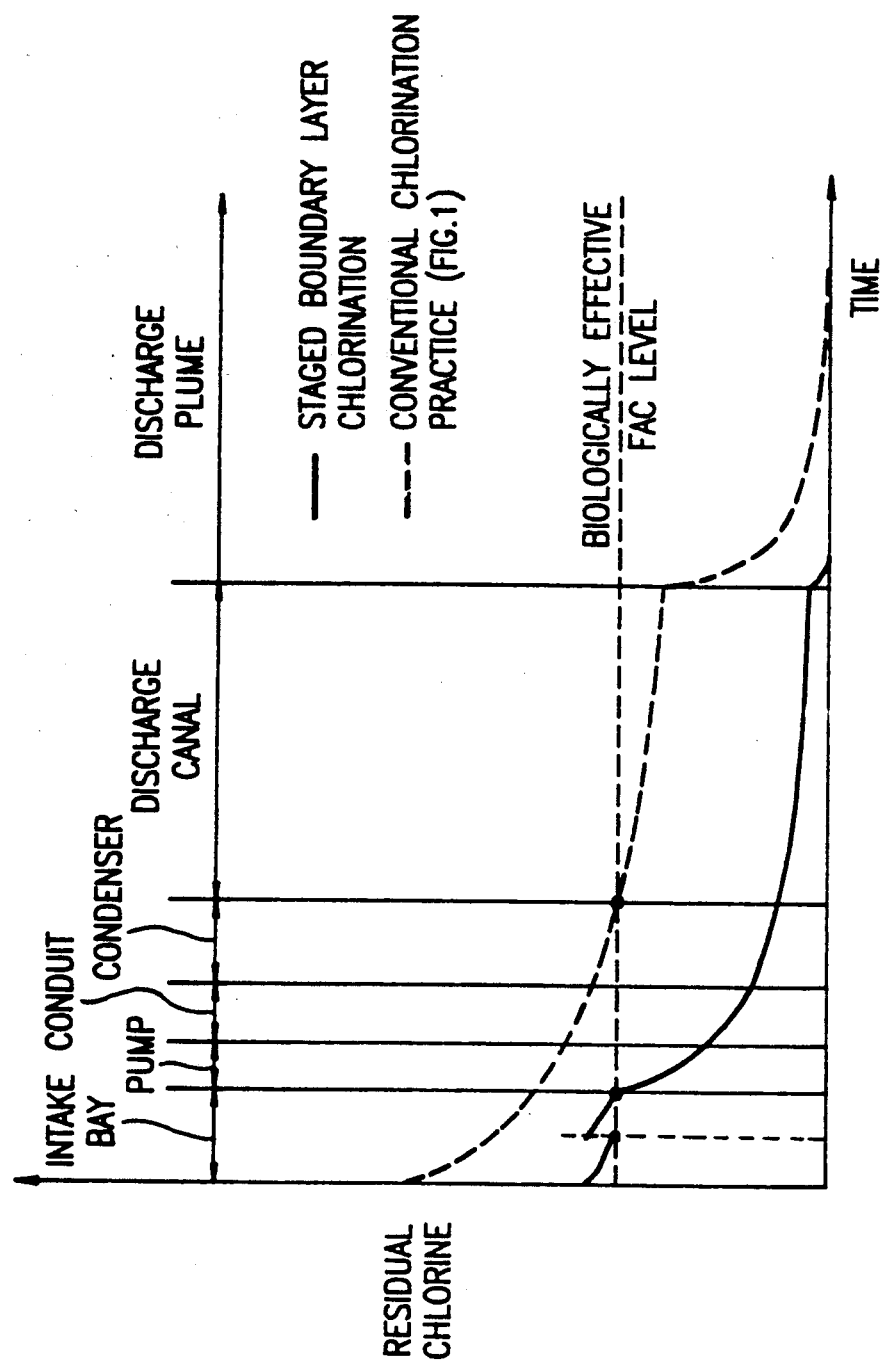
FIG. 6 is a graph comparing the variation of residual chlorine concentrations, in a power plant cooling system, of the system of the present invention and that of the conventional system of FIG. 1.

FIG. 6 shows the spatial variation of residual chlorine concentrations in the cooling system of a power plant for the case of two-stage boundary layer chlorination. By the time the chlorine reaches the discharge outlet, where residual levels are measured, concentrations should be very low or undetectable.

The following is a discussion of theoretical background of the staged boundary layer chlorination technique according to the invention.

Figure 7:
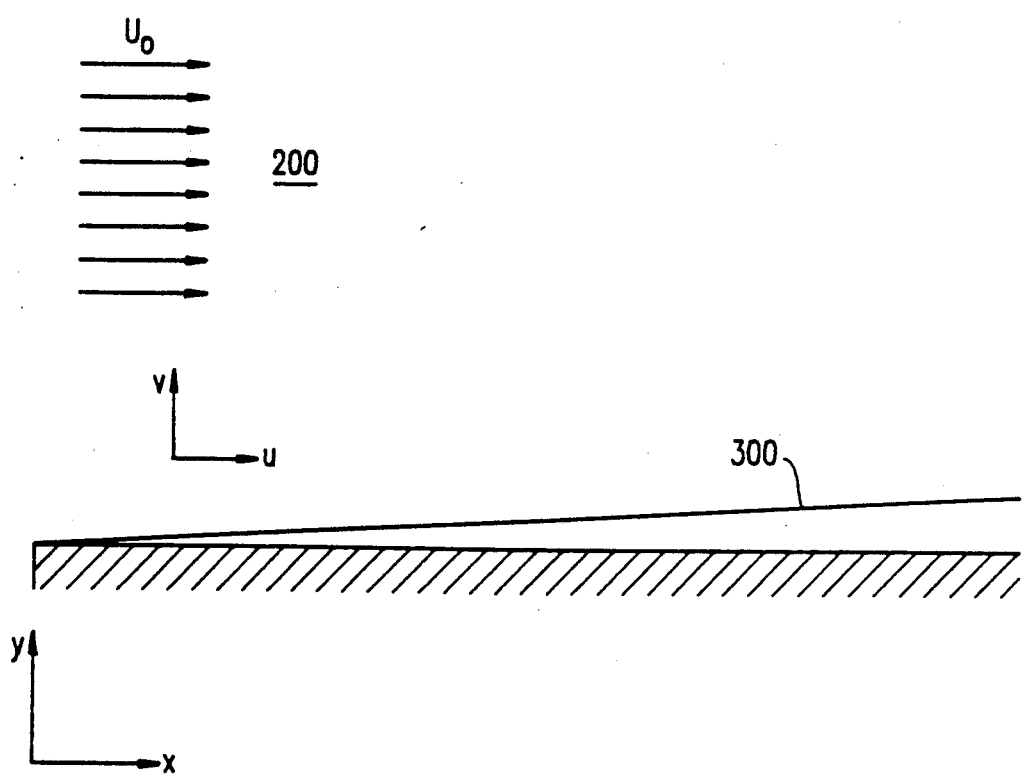
FIG. 7 is a schematic illustration of two regions of fluid flow in an x-y coordinate system.

The basic ideas underlying the approximations that yield the boundary layer theory were developed by Prandtl about 1904. The essential idea is to divide a flow into two major parts. The larger part concerns a free stream of fluid, far from any solid surface, which is accurately considered to be inviscid (irrotational). The smaller part is a thin layer next to a solid surface in which the effects of molecular transport (viscosity, thermal conductivity, and mass diffusivity) are considered at the expense of some approximations. FIG. 7 is a schematic illustration illustrating the two regions of the flow in an x-y coordinate system.

Transport equations for 2-D steady laminar flow are the following:

Continuity: $\frac{\partial u}{\partial x} + \frac{\partial v}{\partial y} = 0$ (1)

Momentum (x — direction): (2)

$$u\frac{\partial u}{\partial x} + v\frac{\partial u}{\partial y} = -\frac{1}{\rho}\frac{\partial p}{\partial x} + \nu\left(\frac{\partial^2 u}{\partial x^2} + \frac{\partial^2 u}{\partial y^2}\right)$$

Momentum (y — direction): (3)

$$u\frac{\partial v}{\partial x} + v\frac{\partial v}{\partial y} = -\frac{1}{\rho}\frac{\partial p}{\partial y} + \nu\left(\frac{\partial^2 v}{\partial x^2} + \frac{\partial^2 v}{\partial y^2}\right)$$

Energy: (4)

$$\rho C_v\left(u\frac{\partial T}{\partial x} + \frac{\partial T}{\partial y}\right) = k\left(\frac{\partial^2 T}{\partial x^2} + \frac{\partial^2 T}{\partial y^2}\right)$$

Concentration: (5)

$$u\frac{\partial C}{\partial x} + v\frac{\partial C}{\partial y} = D\left(\frac{\partial^2 C}{\partial x^2} + \frac{\partial^2 C}{\partial y^2}\right) + S$$

where:
u: Fluid velocity in x-direction
v: Fluid velocity in y-direction
p: Pressure
T: Temperature
C: Concentration
$\nu$: Dynamic viscosity
k: Thermal Conductivity
D: Diffusivity
$\rho$: Density
$C_v$: Specific heat; and
where in Equation (5)

$$\left(u\frac{\partial C}{\partial x} + v\frac{\partial C}{\partial y}\right)$$

is a term indicative of convection transport, i.e., transport on a macroscale, $$\left(D\left(\frac{\partial^2 C}{\partial x^2} + \frac{\partial^2 C}{\partial y^2}\right)\right)$$

is a term indicative of diffusion transport, i.e., transport due to molecular contact, and S is the source/sink term.

The following is a discussion of boundary layer approximations. The influence of molecular transport is confined to an extremely thin region very close to the solid surface. The boundary layer as is defined is the one in which there are large lateral changes and slow longitudinal changes in flow properties. Therefore:

$$u >> v$$
$$\frac{\partial}{\partial y} >> \frac{\partial}{\partial x}$$

Boundary Layer equations then take the following form:

Continuity: $\frac{\partial u}{\partial x} + \frac{\partial v}{\partial y} = 0$ (6)

Momentum (x — direction): (7)

$$u\frac{\partial u}{\partial x} + v\frac{\partial u}{\partial y} = -\frac{1}{\rho}\frac{\partial p}{\partial x} + \nu\frac{\partial^2 u}{\partial y^2}$$

Energy: (8)

$$\rho C_v \left( u \frac{\partial T}{\partial x} + v \frac{\partial T}{\partial y} \right) \simeq k \frac{\partial^2 T}{\partial y^2}$$

Concentration: (9)

$$u \frac{\partial C}{\partial x} + v \frac{\partial C}{\partial y} \simeq D \frac{\partial^2 C}{\partial y^2} + S$$

Similar expressions can be developed for the turbulent flow, where the total viscosity, conductivity and diffusivity will replace the molecular viscosity, conductivity and diffusivity. For example: Total Viscosity = Molecular Viscosity + Turbulent Viscosity The thickness of the boundary layer can then be calculated as follows:

$$\text{Laminar Flow:} \quad \frac{\delta_u}{x} = \frac{5}{\sqrt{Re_x}} \quad (10)$$

$$\text{Turbulent Flow:} \quad \frac{\delta_u}{x} = \frac{0.381}{\sqrt{Re_x^{.02}}} \quad (11)$$

and:

$$\frac{\delta_T}{\delta_u} \simeq Pr^{-1/3} \quad (12)$$

$$\frac{\delta_C}{\delta_u} \simeq Sc^{-1/3} \quad (13)$$

where:

$$Re_x = \text{Reynolds number} = \frac{U_o x}{\nu}$$

$$Pr = \text{Prandtl number} = \frac{\nu}{\alpha} = \frac{C_p \mu}{k}$$

$$Sc = \text{Schmidt number} = \frac{\nu}{D}$$

$$Le = \text{Lewis number} = \frac{\alpha}{D} = \frac{Sc}{Pr}$$

Figure 8A:
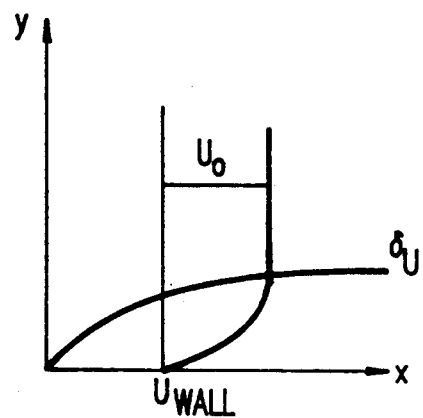
FIGS. 8a, 8b and 8c are graphs illustrating the momentum, temperature and concentration boundary layers, respectively, of fluid flow shown in FIG. 7.
Figure 8B:
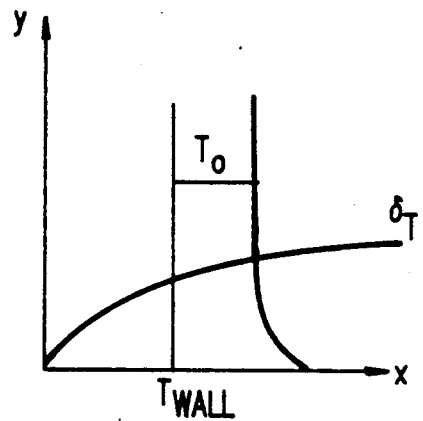
Figure 8C:
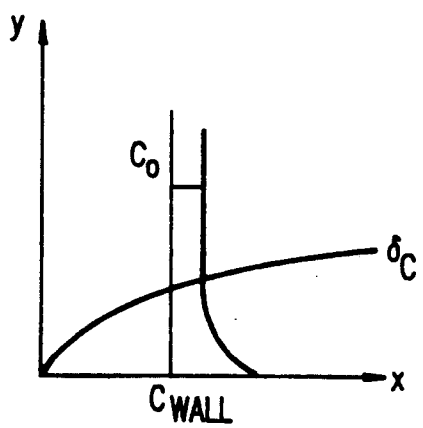

Where:
$U_o$ = freestream velocity
$\alpha$ = thermal conductivity
$C_p$ = specific heat at constant pressure
$\mu$ = kinematic viscosity FIGS. 8a, 8b and 8c are graphic illustrations of the momentum boundary layer $\delta_u$, the temperature boundary layer $\delta_T$ and the concentration boundary layer $\delta_C$. The thickness of momentum boundary layer $\delta_u$ is defined as the distance from the wall where the velocity in the boundary layer reaches 99% of the free stream velocity. Similarly, $\delta_T$ is the thickness of the temperature boundary layer and is defined as the distance from the wall where the temperature boundary layer reaches 99% of the temperature in the free stream. The thickness of the concentration boundary layer $\delta_C$ is defined as the distance from the wall where the concentration in the boundary layer reaches 99% of the concentration in the free stream.

The following is an illustrative example. Consider the intake bay of a power plant which is 40 feet long, 25 feet deep and 12 feet wide. The average water velocity in the bay is:

$U_o = 0.3 m/s$

The thickness of the momentum boundary layer is tabulated below

| x [ft] | $\delta_u$ [inches] |
|--------|---------------------|
| 0      | 0                   |
| 5      | 1.68                |
| 10     | 2.88                |
| 15     | 4.00                |
| 20     | 5.09                |
| 25     | 6.08                |
| 30     | 7.07                |
| 35     | 7.97                |
| 40     | 8.87                |

The total volume $V_{BL}$ occupied by the boundary layer is calculated as $$V_{BL} = \int_A \delta_u dA$$

In this example the boundary layer on the walls of the intake occupies approximately 8 percent of total water volume in the bay.

The thickness of the concentration boundary layer can be determined from:

$$\delta_C \simeq Sc^{-\frac{1}{3}} \delta_u$$

Assuming Le = 1 gives the result (with Pr of water = 6.78): $\delta_C \simeq \frac{1}{2} \delta_u$ This means that the concentration boundary layer (for Le = 1) will be twice thinner than the momentum boundary layer, i.e. it would occupy approximately 4 percent of total water volume in the bay. Staged injection will reduce the volume of the concentration boundary layer even more.

The above result concerning the concentration boundary layer is valid for the case where the mass transfer between the fluid and the surface takes place.

For the typical power plant intake bay, the intake cooling water flows at a rate of 150,000 gal/min. If it is assumed that no chlorine demand reaction takes place and that a 0.1 ppm FAC residual at the pump inlet is to be maintained, $150,000 \times 10^{-7}$ gal/min of chlorine would be required for conventional chlorination. Due to demand reaction losses, it is considered that 10–20 times more chlorine would be required than the above-noted theoretical dose. It is anticipated that the staged chlorination technique of the present invention would reduce the total amount of chlorine by a factor of 10. Assuming two stages of chlorination, and injectors in each chlorination stage, the present invention would then require a chlorination dose at each stage of injectors of $150,000 \times 10^{-7} \times 1/10 \times \frac{1}{2}$ gal/min chlorine per stage. Assuming n injectors per stage, each injector would then inject $1/n \times 7,500 \times 10^{-7}$ gal/min of chlorine, again assuming no demand reactions. Since in the present invention chlorine transport in the boundary layer is controlled mainly by diffusion, compared to the conventional techniques in which free stream transport is dominated by convection, it is anticipated that losses due to demand reaction will be significantly reduced by the present invention. Thus, it is anticipated that the above analysis is conservative.

The preferred embodiment shown in FIG. 5 is more complex because chlorine is injected into the boundary layer as a jet from a point source. It is not anticipated that such method of injection will affect significantly the momentum boundary layer, but it might affect the thickness of the concentration boundary layer, since the above results apply to a distributed source and not to point source. For point source injection, it is anticipated that the thickness of the concentration boundary layer $\delta_C$ might approach the thickness of the momentum boundary layer $\delta_u$.

Figure 9A:
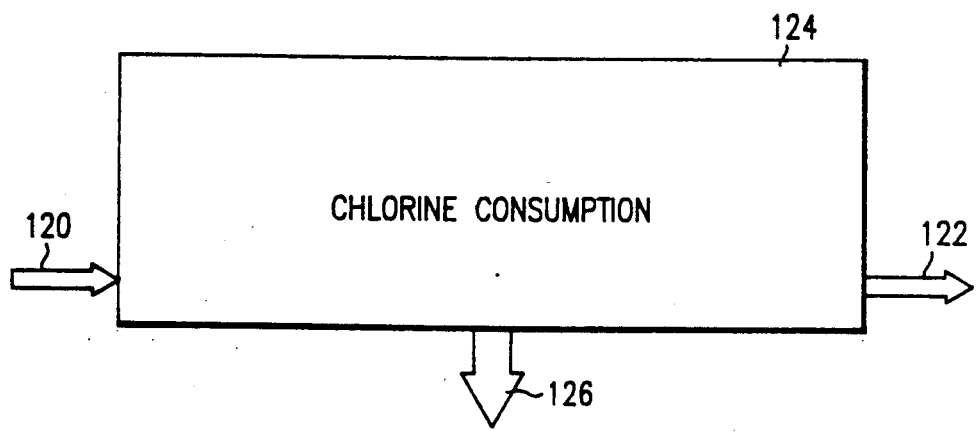
FIGS. 9a and 9b are schematic illustrations of chlorine transport in the conventional chlorination practice and according to the present invention, respectively.

Recapitulating, in the conventional chlorination practice, chlorine is injected at some location downstream of the traveling water screens and the total chlorine residual (TRC) is maintained either at the condenser outlet, conduit inlet, or pump inlet. Transport downstream is primarily through convection, as schematically shown in FIG. 9a. Chlorine is consumed in natural chlorine demand reactions. For this case, chlorine consumption (loss) is proportional to the entire volume of water in the bay. Therefore, the applied chlorine dose and the amount of produced chloramines are large.

Figure 9B:
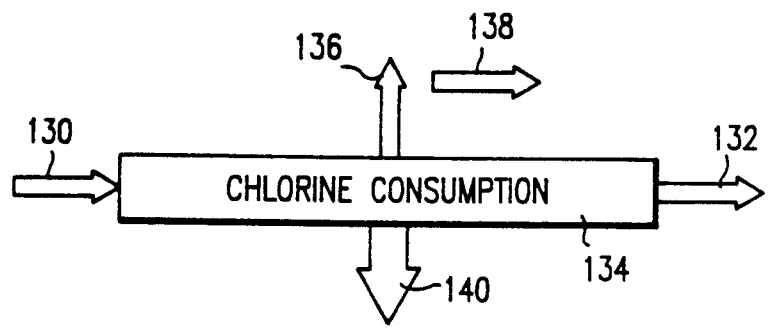

In contrast, according to the present invention, chlorine is injected in stages into boundary layer, and the free chlorine residual is maintained in the boundary layer upstream of the next injection stage. Chlorine is consumed in natural chlorine demand reactions. This consumption is proportional to the volume of boundary layer between two injection points. For a two-stage injection, this volume is approximately 4 percent of total water volume in the intake bay. Therefore, the applied chlorine dose is small. The amount of produced chloramines is also small. Downstream transport, as shown schematically in FIG. 9b, is primarily through convection and diffusion. Some amount of chlorine is also transported into the free stream by the transverse diffusion and convection. Since, in the free stream, the downstream convection is much larger than the transverse diffusion, it is anticipated that the most of that chlorine will be convected downstream. As a consequence, this method of chlorine injection will result in high chlorine concentrations near the wall and low concentrations in the free stream.

The staged boundary layer chlorination technique offers unique possibility for achieving macrobiofouling control in the intake structure of the power plant, while having undetectably low or very low chlorine residuals in the discharge at the compliance point. The staged boundary layer chlorine injection is superior to current chlorination practices for the following reasons:

Distance between the injection point and the point where the residual is maintained is significantly shorter, thus resulting in a significant decrease in chlorine losses and, consequently, a decrease in the specific chlorine dose.

Only the boundary layer near the wall is treated with the full dose. As a result, the absolute chlorine dose is significantly lower.

The chlorine residual at the compliance point is considerably lower due to large dilution of the treated boundary layer with the main cooling water flow, and due to the biological demand for chlorine in the condenser.

The advantage of staged boundary layer chlorination, compared to other control techniques, is that no expensive mussel filters or dual-flow screens in a no-well arrangement are necessary. It would be sufficient to modify the existing traveling screens and to protect the condenser tubes from debris carryover. Clam traps or screen panels, installed in the condenser inlet water box, could be used for this purpose.

On Nov. 19, 1982, the U.S. Environmental Protection Agency (EPA) published revised federal effluent limitation guidelines for steam-electric generating facilities. Total residual chlorine (TRC) in once-through cooling water discharges for the main condenser was limited to a daily maximum of 0.2 mg/l applied at the NPDES discharge point to the receiving body of water. There is no average chlorine limitation and each power plant unit may not discharge chlorine for more than two hours per day. Exceptions apply if the facility owner demonstrates to the regulatory agency that there is a need for a longer duration of chlorination in order to control macroinvertebrates.

One of the biggest changes for once-through cooled power plants is regulation of TRC instead of FAC. Free available chlorine is the only part of TRC which provides effective biofouling control within short residence times in power plant cooling systems. Therefore, there is no way to guarantee chlorination effectiveness based on entirely of TRC. A concern among the utilities is that if chlorine use is reduced to meet the 0.2 mg/l TRC limit, biofouling control will not be effective. Some utilities had to install dechlorination systems to facilitate the necessary biofouling control and to meet permit limits.

The major impact of the EPA regulations on power plant operation is decreased effectiveness of conventional chlorination, with a concomitant decrease in performance and increase in operation and maintenance costs; if biofouling becomes severe enough, unit availability will suffer, and replacement power costs also must be considered.

By minimizing dilution losses and losses due to the natural chlorine demand reactions, the staged boundary layer chlorination injection technique will result in a significant reduction in applied chlorine dose (both the specific and absolute chlorine dose). It will thus offer a unique possibility for achieving macrobiofouling control in the intake structure of a power plant, while having acceptably low chlorine residuals in the cooling water discharges at the NPDES compliance point. The staged boundary layer chlorine injection will, therefore, have a positive effect on unit availability, performance, and operation and maintenance costs.

Further, although the above discussion assumes use of chlorine as a biofouling control agent, the principles on which the present invention is based certainly are not limited to the use of chlorine. Indeed, $O_3$, BrCl, $ClO_2$, other bromine salts and other generally available organic and inorganic toxicants can be used. Further, hot water or steam can also be used to maintain the temperature at the measurement points in the boundary layer at 100° F. or higher, thereby also serving as an effective biofouling control agent. A particularly attractive embodiment for biofouling control in a power plant intake structure is to feed back from the output of the power plant condenser heated water or steam extracted from the turbine cycle to the injectors of the several injection stages, with the amount of heated water/steam fed back being controlled based on the temperature measured in the boundary layer at the various measurement points.

Further advantageous embodiments of the present invention are possible based on the above teachings. For example, different control agents more effective for different purposes could be used at different injector stages, or even at the same injector stage. Insofar as chlorine is a more effective control agent at higher temperatures, the present invention includes injecting chlorine and hot water/steam either from separate nozzles or by means of a nozzle within a nozzle arrangement, at one or more injector stages. Clearly, also, chlorine could be injected in the hot water/steam fed back from the output of the power plant condenser/turbine cycle. Temperature and chlorine concentration would then both be control parameters measured at the measurement points, with each used to control, respectively, the amount of hot water/steam and chlorine injected. In yet another variation taking advantage of seasonal differences in biofouling conditions, the present invention envisions using the several injection stages to inject one control agent, such as chlorine, during peak biofouling seasons and another biofouling control agent during off-peak seasons.

While the above disclosure particularly address biofouling in the intake structure of a power plant, the present invention is applicable to all fluid containing structures susceptible to biofouling, including process industries such as paper mills and chemical industries.

Obviously, numerous additional modifications and variations of the present invention are possible in light of the above teachings. It is therefore to be understood that within the scope of the appended claims, the invention may be practiced otherwise than as specifically described herein.

WHAT IS NEW AND DESIRED TO BE SECURED BY LETTERS PATENT OF THE UNITED STATES IS:

1. A method for biofouling control in a fluid containing structure susceptible to biofouling, comprising:
   injecting a first biofouling control agent into a boundary layer adjacent walls of said fluid containing structure at a first injection stage;
   injecting a second biofouling control agent into the boundary layer adjacent said walls of said fluid containing structure at a second stage downstream of said first stage;
   measuring at least a first control parameter associated with said first control agent upstream of said second stage;
   controlling injecting of said first control agent at said first injection stage based on the measured first control parameter;
   measuring at least a second control parameter associated with said second control agent downstream of said second stage; and
   controlling injecting of said second control agent at said second stage based on the measured second control parameter.

2. The method according to claim 1, wherein each said measuring step comprises measuring said first and second control paramaeters in said boundary layer.

3. The method according to claim 2, wherein each injection stage comprises plural injectors arranged in the boundary layer at locations defining a plane perpendicular to fluid flow, comprising:
   performing each injecting step by injecting said first and second control agents in said boundary layer by means of said plural injectors.

4. The method according to claim 3, comprising:
   performing at least one of said measuring steps by means of plural sensors arranged in a plane perpendicular to fluid flow; and
   controlling injecting by the injectors of the respective injection stage controlled by said plural sensors by assigning selected injectors to respective sensors and controlling injection by the selected injectors based on the control parameter measured by the respective sensors.

5. The method according to claim 3, comprising:
   performing at least one of said measuring steps by means of plural sensors arranged in a plane perpendicular to fluid flow;
   determining an average of the control parameter measured by from said plural sensors; and
   controlling injecting by the injectors of the respective injection stage controlled by said plural sensors based on the determined average.

6. The method according to claim 3, comprising:
   performing at least one of said measuring steps by means of plural sensors arranged in a plane perpendicular to fluid flow;
   determining for each injector of the associated injection stage controlled by said plural sensors a weighted average of the control parameter measured by said plural sensors; and
   controlling injecting by each injector of said respective injection stage controlled by said plural sensors based on the respectively determined weighted average.

7. The method according to claim 1, wherein at least one of said first and second injecting steps comprises:
   injecting as said first and second control agents a fluid selected from the group consisting of Cl, $H_2O$ at elevated temperature, $O_3$, $ClO_2$, dissolved bromine salts, and combinations thereof.

8. The method according to claim 1, wherein at least one of said first and second injecting steps comprises:
   injecting water at a sufficiently high temperature so that the temperature of the boundary layer measured in the respective measuring steps is higher than the free flow temperature by a predetermined amount.

9. The method according to claim 8, wherein at least one of said first and second injecting steps further comprises:
   injecting a fluid selected from the group consisting of Cl, $O_3$, $ClO_2$, dissolved bromine salts and combinations thereof.

10. A system for biofouling control in a fluid containing structure susceptible to biofouling, comprising:
    a first injection stage means for injecting a first biofouling control agent into a boundary layer adjacent walls of said fluid containing structure;
    a second injection stage means downstream of said first stage means for injecting a second biofouling control agent into the boundary layer adjacent said walls of said fluid containing structure downstream of said first stage means;
    first measuring means for measuring at least a first control parameter associated with said first control agent upstream of said second stage means;
    first control means for controlling injecting of said first control agent at said first injection stage means based on the measured first control parameter measured by said first measuring means;
    second measuring means for measuring at least a second control parameter associated with said second control agent downstream of said second stage means; and second control means for controlling injecting of said second control agent at said second stage means based on the measured second control parameter measured by said second measuring means.

11. The system according to claim 10, wherein said first and second measuring means include sensors located in said boundary layer.

12. The system according to claim 11 wherein each injection stage means comprises plural injectors arranged in the boundary layer at locations defining a plane perpendicular to fluid flow.

13. The system according to claim 12, comprising:
at least one of said first and second measuring means comprising plural sensors arranged in a plane perpendicular to fluid flow; and
the respective of said first and second control means including means for assigning selected injectors to respective of said sensors and controlling injection by the selected injectors based on control parameters measured by the respective sensors.

14. The system according to claim 12, comprising:
at least one of said first and second measuring means comprising plural sensors arranged in a plane perpendicular to fluid flow;
means for determining an average of the control parameters measured by said plural sensors; and
the respective of said first and second control means controlling injecting by the injectors of the respective injection stage means controlled by said plural sensors based on the determined average.

15. The system according to claim 12, comprising:
at least one of said first and second measuring means comprising plural sensors arranged in a plane perpendicular to fluid flow;
means for determining for each injector of the associated injection stage means controlled by said plural sensors a weighted average of the control parameters measured by said sensors; and
the respective of said first and second controlling means controlling injecting by each injector of said respective injection stage means controlled by said plural sensors based on the respectively determined weighted average.

16. The system according to claim 10, wherein said first and second injection stage means inject as said first and second control agents a fluid selected from the group consisting of Cl, $H_2O$ at elevated temperature, $O_3$, $ClO_2$, dissolved bromine salts and combinations thereof.

17. The system according to claim 10, wherein at least one of said first and second injection stage means comprises means for injecting water at a sufficiently high temperature so that the temperature of the boundary layer as measured by the respective measuring means is elevated by a predetermined amount relative to the free flow temperature.

18. The system according to claim 17, wherein at least one of said first and second injection stage means includes means for injecting a fluid selected from the group consisting of Cl, $O_3$, $ClO_2$, dissolved bromine salts and combinations thereof.

* * * * *